(12) United States Patent
Ongaro et al.

(10) Patent No.: US 9,186,429 B2
(45) Date of Patent: Nov. 17, 2015

(54) STEAM STERILIZER

(75) Inventors: Daniele Ongaro, Villa di Serio (IT); Mariapia Ghilardi, Villa di Serio (IT)

(73) Assignee: ABSOLUTE UP S.R.L., Villa di Serio (BG) (IT)

( * ) Notice: Subject to any disclaimer, the term of this patent is extended or adjusted under 35 U.S.C. 154(b) by 0 days.

(21) Appl. No.: 14/237,080

(22) PCT Filed: May 28, 2012

(86) PCT No.: PCT/IB2012/052658
§ 371 (c)(1),
(2), (4) Date: May 16, 2014

(87) PCT Pub. No.: WO2013/021293
PCT Pub. Date: Feb. 14, 2013

(65) Prior Publication Data
US 2014/0248180 A1 Sep. 4, 2014

(30) Foreign Application Priority Data
Aug. 5, 2011 (IT) .............................. MI2011A1507

(51) Int. Cl.
| | | |
|---|---|---|
| A61L 2/00 | (2006.01) | |
| A61L 9/00 | (2006.01) | |
| A61L 2/26 | (2006.01) | |
| A61L 2/07 | (2006.01) | |
| F28D 1/02 | (2006.01) | |
| F28D 21/00 | (2006.01) | |

(52) U.S. Cl.
CPC ... *A61L 2/26* (2013.01); *A61L 2/07* (2013.01); *F28D 1/0213* (2013.01); *F28D 21/0001* (2013.01)

(58) Field of Classification Search
CPC ..................................... A61L 2/00; A61L 2/07
USPC ........................... 422/26, 292, 298, 305, 307
See application file for complete search history.

(56) References Cited

FOREIGN PATENT DOCUMENTS

| | | | |
|---|---|---|---|
| GB | 1 555 295 A | 11/1979 | |
| GB | 1555295 | * 11/1979 | ................ A61L 3/00 |
| WO | 02/096472 A1 | 12/2002 | |

OTHER PUBLICATIONS

International Search Report for International Application No. PCT/IB2012/052658; two pages; mailed Oct. 17, 2012.

* cited by examiner

*Primary Examiner* — Monzer R Chorbaji
(74) *Attorney, Agent, or Firm* — Vorys, Sater, Seymour and Pease LLP; Ari G. Zytcer

(57) ABSTRACT

Provided is a steam sterilizer for medical instruments comprising a feeding system configured to move a sterilization fluid; a discharge system configured to move a waste fluid and including a discharge tank configured to collect the waste fluid; a cooling apparatus for cooling said waste fluid and including a cooling means configured to cool the waste fluid when it is inside said discharge tank.

5 Claims, 1 Drawing Sheet

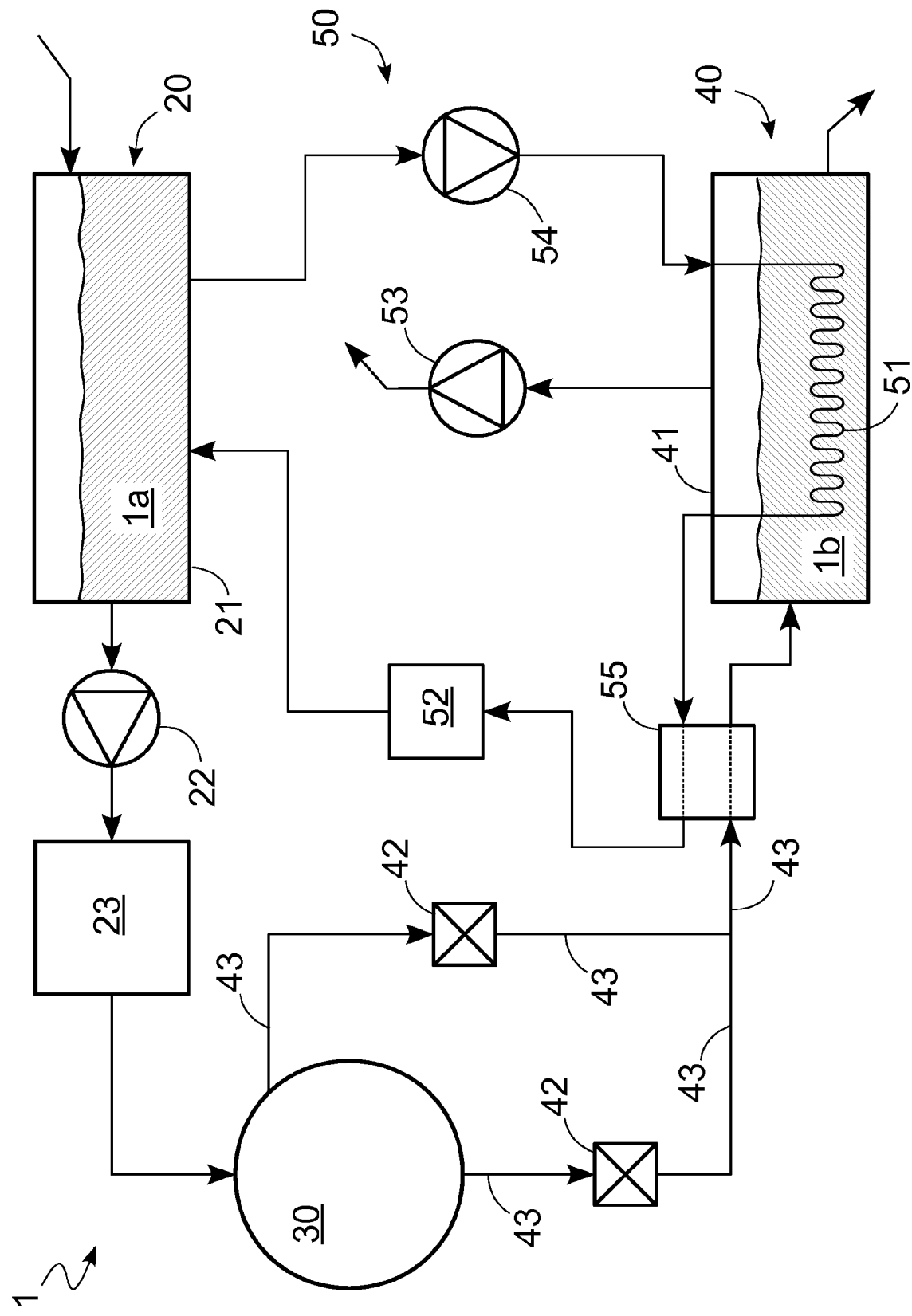

STEAM STERILIZER

The present invention relates to a steam steriliser of the type pointed out in the preamble of the first claim.

In detail, the invention relates to a steam steriliser adapted to sterilise/disinfect surgical and/or medical-dental instruments, in the following merely referred to as "medical instruments", through use of high-temperature and high-pressure saturated steam.

It is known that, during any operation, in order to avoid arising of infections or other similar problems, availability of medical instruments characterised by a high sterilisation degree is of the greatest importance.

To this aim, several types of sterilisers have been conceived that, based on different techniques, enable good sterilisation/disinfection of said instruments to be achieved.

A first example of these sterilisers is represented by chemical sterilisers that, to carry out disinfection, use chemical substances such as ethylene oxide or ethoxide.

Another type of sterilisers is represented by plasma sterilisers that carry out sterilisation of medical instruments through exploitation of a gas, such as hydrogen peroxide, brought to the plasma state.

These two types of sterilisers, while ensuring a good sterilisation coefficient, are scarcely employed because the substances therein used tend to form residues on the instruments themselves. In particular, as these residues can cause infections or other similar problems in patients, they are removed by submitting the instruments to deep and intense residue-removal rinsing operations, which on the other hand gives rise to increase in costs and decay in sterilisation.

A further type of sterilisers is represented by sterilisers in which radiation is used (ultraviolet radiation, γ rays or microwaves) to carry out disinfection of the medical instruments.

These sterilisers too, due to the high costs both for manufacturing and using these devices are scarcely employed.

For the above reasons, the most adopted sterilisers are steam sterilisers, also referred to as autoclaves, that, unlike the preceding ones, have particularly reduced manufacturing and use costs and, above all, are of simple use and also can be easily positioned in laboratories due to their reduced sizes.

Presently known steam sterilisers consist of a main tank containing water (demineralised water, for example); a sterilisation chamber inside which the instruments to be sterilised are placed; a supply system adapted to draw water from the main tank and convert it into steam and carry it to the sterilisation chamber; drying means adapted to dry the instruments through a hot air jet, for example; and a discharge apparatus adapted to evacuate the waste fluid, i.e. the residual liquid and gas/steam from the sterilisation process.

Some examples of these steam sterilisers are described in patents U.S. Pat. No. 5,348,711 A, GB 1235952 A and U.S. Pat. No. 6,379,613.

Steam sterilisers are further provided with a cooling system for the waste fluid which is necessary to meet suitable safety requirements to both facilitate and speed up full emptying of the sterilisation chamber and, therefore, subsequent re-use of the steriliser.

The cooling system has a discharge duct drawing the waste fluid from the sterilisation chamber and bringing it to a heat exchanger, usually air, where it is submitted to cooling, being then collected in a suitable discharge tank.

Another type of cooling system contemplates use of a duct bringing the waste fluid from the sterilisation chamber to the main tank where, through a suitable cooling pipe coil, said waste fluid transfers heat to the sterilisation fluid and is then collected in a suitable discharge tank or directly released into the main tank where it is mixed with said sterilisation fluid.

In a further cooling system the outgoing fluid is provided to be mixed with water from a supply external to the steriliser, such as the waterworks of the building where the steriliser itself is placed and used.

Some examples of steam sterilisers provided with a cooling system are described in patents US 20110076192 A1, GB 2320433 A and U.S. Pat. No. 5,505,056.

The known art mentioned above has some important drawbacks.

In fact, known steam sterilisers and in particular known cooling systems are characterised by poor efficiency.

In particular, said first cooling system, as it only works during discharge of the sterilisation chamber, has running costs particularly high due to the necessity of a heat exchanger that, as it must cool the fluid within a reduced period of time, is characterised by high power and therefore, high energy consumption.

In the second known cooling system, the poor efficiency is caused by the temperature of the sterilisation fluid that, after each cycle, tends to rise thus impairing efficiency and yield of the whole steriliser.

In addition, should the discharge fluid be discharged into the main tank, decay of the sterilisation fluid can occur so that said fluid does not ensure correct disinfection of the instruments any more.

These problems of poor efficiency can further be also found in the third cooling system described above where, due to the strong use of water from the external system, costs are greatly increased.

Under this situation, the technical task underlying the present invention is to conceive a steam steriliser capable of substantially obviating the mentioned drawbacks.

Within the scope of this technical task, it is an important aim of the invention to provide a steam steriliser characterised by reduced both manufacturing and running costs.

Another important aim is to obtain a steam steriliser characterised by a particularly efficient cooling system.

In particular, the invention aims at manufacturing a steam steriliser having a cooling system capable of disposing of the waste fluid with reduced energy consumption.

The technical task and the aims specified are achieved by a steam steriliser as claimed in the appended claim 1.

Preferred embodiments are highlighted in the subclaims.

The features and advantages of the invention are hereinafter clarified by the detailed description of a preferred embodiment of the invention, with reference to the accompanying FIG. 1 showing the steam steriliser in accordance with the invention.

With reference to the mentioned drawing, the steam steriliser according to the invention is generally identified by reference numeral 1.

It substantially consists of a sterilisation plant for medical instruments and, in particular medical-dental instruments and the like that, for carrying out said sterilisation, use a sterilisation fluid 1$a$, usually demineralised water, in the steam state and characterised by high pressure and temperature values.

Briefly, the steam steriliser 1 comprises a feeding system 20 adapted to move and treat the sterilisation fluid 1$a$; a sterilisation chamber 30 inside which the medical instruments are disposed and sterilised; a discharge system 40 adapted to cause movements in the waste fluid 1$b$ once sterilisation is over, and to evacuate it from chamber 30.

In detail, the feeding system 20 comprises a main tank 21 adapted to be brought into connection for fluid passage with an outer supply system and to store the sterilisation fluid 1$a$;

at least one first pump 22 adapted to move the fluid between said tank 21 and sterilisation chamber 30; and a vaporisation unit 23, known by itself and diagrammatically shown in FIG. 1, adapted to convert the fluid from a liquid state to the steam state.

The main tank 21 is provided with first measuring means adapted to measure the volume and pressure of the sterilisation fluid 1a contained in tank 21 so as to determine a minimum level and a maximum level of the fluid 1a volume and pressure.

The sterilisation chamber 30 consists of a sterilisation chamber of reduced volume for medical instruments and, preferably, dental instruments and the like. It is known by itself and is usually made up of a structure having an almost cylindrical shape and made of stainless steel.

The discharge system 40 comprises a discharge tank 41 adapted to store the discharge fluid 1b coming out of the sterilisation chamber 30 and adapted to be brought into connection for fluid passage with an outer discharge system; one or more solenoid valves or electrovalves 4 adapted to move the waste fluid 1b from the sterilisation chamber 30 to the discharge tank 41; a series of discharge ducts 43 adapted to bring into connection for fluid passage said discharge tank 41 with the sterilisation chamber 30.

The discharge tank 41, in the same manner as the main tank 21, is provided with second measuring means adapted to measure the volume and pressure of the waste fluid 1b contained in said tank 41 so as to determine a minimum level and a maximum level of the fluid 1b volume and pressure.

Preferably, the main tank 21 and discharge tank 41 substantially have the same capacity and a capacity of about 4 litres, for example.

The steam steriliser 1 is finally advantageously provided with a cooling apparatus 50 adapted to cool the waste fluid 1b present in the discharge system 40.

The cooling apparatus 50 comprises a cooler 52 adapted to cool the cooling liquid, and cooling means adapted to cool the waste fluid 1b when it is inside tank 41.

In particular, the cooling means can be an indirect heat exchanger 51 adapted to carry out heat exchange between a cooling liquid and the waste fluid 1b.

In addition to the exchanger 51, said means can be a vacuum pump 53 adapted to put the discharge tank 41 under vacuum so that, as hereinafter better described, lowering of the temperature of the waste fluid 1b contained in the discharge tank 41 is promoted. In another alternative, said cooling means can comprise both the indirect heat exchanger 51 and the vacuum pump 53. Said vacuum pump 53, in addition to having said cooling function, can be used to put the discharge system 40 under vacuum so as to promote evacuation of chamber 20.

The cooling liquid preferably consists of the sterilisation fluid 1a and, therefore, the cooling apparatus 50, as shown in FIG. 1, has a series of ducts adapted to mutually bring into connection for fluid passage the different components of apparatus 50 and tanks 21 and 41, and an actuating pump 54 adapted to move the cooling fluid 1a inside said ducts between the two tanks 21 and 41.

The indirect heat exchanger 51 is made up of any heat exchanger in which passage of heat between the fluids 1a and 1b occurs by indirect conduction. In detail, the expression indirect heat exchanger therefore identifies a heat exchanger in which passage of heat between two fluids takes place without direct contact between them and, therefore, through a suitable exchange surface enabling the fluids not to be mixed with one another.

Preferably, the indirect heat exchanger 51 consists of an indirect surface heat exchanger in which fluids 1a and 1b are caused to flow inside two separate chambers so that passage of heat between the fluids 1a and 1b takes place through the wall separating the two fluids. Still more preferably, the two fluids 1a and 1b are adapted to pass through the indirect heat exchanger 51 with flows having opposite ways through said chambers.

The indirect heat exchanger 51 is integrated into the discharge tank 41 and, in particular, it is suitably disposed inside the tank 41 itself. In detail, the heat exchanger 51 is made up of a pipe coil disposed inside the discharge tank 41 so as to be dipped in the discharge fluid 1b and passed through by the sterilisation fluid 1a.

The cooler 52, as shown in FIG. 1, is interposed between the indirect heat exchanger 51 and main tank 21 so as to enable the sterilisation fluid 1a to cool before coming back to the inside of the main tank 21.

It preferably consists of an air cooler having a finned pipe coil, i.e. characterised by a high outer surface which is internally passed through by the sterilisation fluid 1a and externally grazed by an air jet adapted to remove heat from the pipe coil and, therefore the sterilisation fluid 1a.

The cooling means can further comprise an additional indirect heat exchanger 55 adapted to exchange heat between the fluids 1a and 1b.

In particular, the additional exchanger 55 is integrated with the discharge ducts 43 so as to enable the waste fluid 1b to be cooled while it moves from the sterilisation chamber 30 to the discharge tank 41. More particularly, as shown in FIG. 1, the additional indirect exchanger 55 is interposed between the indirect heat exchanger 51 and cooler 52.

As an alternative, the additional indirect heat exchanger 55 can be integrated into the main tank 21. In detail, in this case the additional exchanger 55 can for example consist of a pipe coil dipped in the sterilisation fluid 1a and adapted to be passed through by the waste fluid 1b that, after coming out of chamber 30, transfers heat to the sterilisation fluid 1a inside tank 21 and, subsequently, reaches the discharge tank.

In a further alternative, the additional indirect exchanger 55 can be integrated into the sterilisation chamber 30 so as to remove heat from the steam present in chamber 20 so that said steam cools and then condenses.

The additional exchanger 55 consists of any heat exchanger in which heat passage between the fluids 1a and 1b occurs by indirect conduction. In detail, the exchanger 55 can be an exchanger of the regeneration type in which, for example, fluids 1a and 1b are alternately sent to the inside of a chamber that, therefore absorbs heat from the hot fluid, i.e. the waste fluid 1b and subsequently releases it to the cooler fluid, i.e. the sterilisation fluid 1a.

As an alternative, the additional exchanger 55 consists of a surface heat exchanger in the same manner as the indirect heat exchanger 51, in which the fluids 1a and 1b are caused to flow into two separate chambers preferably having opposite travel ways.

The cooling apparatus 50 can finally be provided with one or more sensors adapted to measure the temperature of the fluids 1a and 1b in the two tanks 21 and 41 and a control box that, based on data supplied from said sensors and the measuring means, adjusts operation of at least apparatus 50.

The steam steriliser 1, described above as regards structure, operates as follows. At the beginning the medical-dental instruments or the like are loaded into the sterilisation chamber 30 that, therefore, can be manually opened and accessible. At this point the sterilisation process begins and, more specifically, the disinfection step begins.

In this disinfection step the vaporisation unit 23, in known manner, draws a given amount of sterilisation fluid 1a from tank 21, vaporises it and then admits it into chamber 30 so as to carry out sterilisation of the instruments.

Once the sterilisation step is over, there is a discharge step in which the electrovalves 42 call the waste fluid 1b back from the sterilisation chamber 30 and admit it into the discharge tank 41. In particular, this discharge step can be also obtained by virtue of the vacuum pump 53 that, putting the discharge system 40 under the vacuum, promotes exit of the waste fluid 1b from the sterilisation chamber 30.

In addition, during the discharge step the waste fluid 1b, reaching tank 41 is admixed with the waste fluid 1b already present in the discharge tank 41 that, having been previously cooled, enables first cooling of the waste fluid 1b having just now reached tank 41 to be carried out.

The cooling apparatus 50 can be activated, therefore causing beginning of the refrigeration step in which heat is removed from the waste fluid 1b at least when it stays inside the discharge tank 41.

In particular, at this point, by activation of the actuating pump 54, start of at least one cooling sub-step is caused or, alternatively, by activation of the vacuum pump 53, starting of a heat-subtraction sub-step occurs.

In a further alternative, pumps 53 and 54 are simultaneously activated so as to carry out both the heat-subtraction sub-step and at least one cooling sub-step almost at the same time.

During the heat-subtraction sub-step, the vacuum pump 53 sucks an air and steam mixture from the discharge tank 41 and discharges it to the outside causing a pressure reduction inside the tank 41 itself and, therefore, in the waste fluid 1b contained therein.

In turn, said pressure lowering causes variation in the boiling point of the waste fluid 1b and, more specifically, reduction in the boiling temperature of the waste fluid 1b that, therefore, increases the spontaneous evaporation rate of the waste fluid 1b itself.

This sucking action causes evaporation of part of the waste fluid 1b that, due to this change of state, subtracts heat from the fluid portion 1b remaining in the liquid state and cooling it.

In addition, the vacuum pump 53 is operated in such a manner as to avoid the balance condition between liquid phase and steam of the waste fluid 1b being reached inside the discharge tank 41, causing interruption of the spontaneous evaporation of the fluid 1b itself and therefore stopping of the heat-subtraction sub-step. To this aim, the vacuum pump 53 can be almost always active or, alternatively, activated at regular given intervals, for example depending on the waste fluid's 1b pressure and temperature inside tank 41.

Simultaneously with the heat-subtraction sub-step, the refrigeration step contemplates provision for at least one cooling sub-step and, preferably, at least one first cooling sub-step.

In this first cooling sub-step, the cooling liquid, i.e. the sterilisation fluid 1a, pushed by the actuating pump 54 starts circulating inside the cooling apparatus 50 starting cooling of the waste fluid 1b. In particular, the sterilisation fluid 1b circulates inside the indirect heat exchanger 51 and therefore subtracts heat by indirect conduction from the waste fluid 1b contained in the discharge tank 41.

In addition, operation of pump 54 and therefore carrying out of the first cooling sub-step can be almost always active or, alternatively, operation of said pump can be started at given regular intervals, depending on the temperature of the waste fluid 1b in tank 41, for example.

Once the sterilisation fluid has come out of the exchanger 51, it reaches the inside of the additional indirect heat exchanger 55.

In particular, if the discharge step is being carried out, in the additional exchanger there is the simultaneous circulation of the waste fluid 1b from the sterilisation chamber 30 and of the sterilisation fluid 1a from the exchanger 51, so that the second cooling sub-step by indirect conduction is started.

In this second cooling sub-step, the waste fluid 1b present in the additional exchanger 55 has a higher temperature than the waste fluid 1b contained in the discharge tank 41 and therefore a higher temperature than the sterilisation fluid coming out of exchanger 51 to which therefore the waste fluid 1b transfers heat.

Once the sterilisation fluid 1a has passed the additional heat exchanger 55, it reaches cooler 52 to which it transfers heat so that it substantially goes back to the same temperature it had at the beginning in the main tank 21.

The invention enables important advantages.

In fact, the steriliser 1 is able to carry out cooling of the waste fluid 1b with high efficiency and effectiveness.

These increases in efficiency and effectiveness have been obtained due to the possibility of removing heat from the waste fluid 1b during particularly long periods of time ensured by the fact that, unlike what happened in known sterilisation operations, the cooling apparatus and, in particular, the vacuum pump 53 and indirect exchanger 51 are able to work without interruption.

This possibility is ensured by the fact that, unlike in known devices where removal takes place during the evacuation time of the sterilisation chamber, heat removal from the waste fluid 1b occurs inside the discharge tank 41, i.e. in a region where the waste fluid remains for a non-limited period of time.

In addition, the possibility of the exchanger 51 working continuously is guaranteed by the measuring means; actually, due to the fact that this means ensures the presence in the main tank of at least one minimum level of sterilisation fluid 1a, it allows an amount of sterilisation fluid 1a required for avoiding failures or other problems to apparatus 50, irrespective of the sterilisation cycles carried out.

The possibility of carrying out both the first cooling sub-step and the heat-subtraction sub-step continuously enables the availability of a cooling apparatus characterised by components of reduced bulkiness, small power and therefore reduced consumption.

An important objective achieved by the present invention is represented by the fact that the overall fluid volume, i.e. the waste fluid 1b plus the sterilisation fluid 1a, is almost constant over the period of time included between two sterilisation cycles, therefore allowing a substantially constant refrigeration capacity to be defined.

This aspect is ensured by the presence in the discharge tank 41 of a waste fluid suitably cooled by the sterilisation fluid and which therefore allows the waste fluid coming from the sterilisation chamber 21 to be cooled as soon as it is admitted into tank 41.

Another important advantage is represented by the fact that, while using the sterilisation fluid 1a as the cooling liquid, it is not submitted to heating, which would cause decay of the steriliser's 1 performances, as it happens in known sterilisers. In fact, the substantial non-heating of the sterilisation fluid allows creation in the sterilisation fluid 1a, due to heating, of the conditions appropriate to growing of the bacterial load to be avoided.

A further advantage is represented by the fact that the sterilisation fluid 1a and waste fluid 1b are never mixed together so that the sterilisation fluid 1a keeps a high purity degree and therefore always ensures optimal disinfection or sterilisation of the medical instruments.

The invention is susceptible of variations falling with the scope of the inventive idea. All of the elements described and claimed can be replaced by equivalent elements and the details, materials, shapes and sizes can be of any nature and magnitude.

The invention claimed is:

1. A steam sterilizer for medical instruments, comprising:
   a sterilization chamber,
   a feeding system configured to move a sterilization fluid from a tank through a vaporization unit to said sterilization chamber,
   a discharge system comprising a discharge tank, said discharge system configured to move a waste fluid from said sterilization chamber to said discharge tank, and said discharge tank being configured to collect said waste fluid;
   a cooling apparatus for cooling said waste fluid; said cooling apparatus comprising an indirect heat exchanger integrated into said discharge tank, configured to cool said waste fluid when said waste fluid is inside said discharge tank;
   ducts configured to mutually bring into connection for fluid passage said tank and said discharge tank;
   an actuating pump configured to move said cooling fluid inside said ducts between said tank and said discharge tank; and
   said steam sterilizer configured to utilize a cooling liquid, the cooling liquid consisting of said sterilization fluid, for removing heat from said waste fluid by indirect conduction.

2. The steam sterilizer as claimed in claim 1, wherein said first indirect heat exchanger is a surface heat exchanger.

3. The steam sterilizer as claimed in claim 1, wherein said discharge system comprises discharge ducts configured to guide said waste fluid into said discharge tank; wherein said cooling means further comprises a second indirect heat exchanger integrated into said discharge ducts and suitable to exchange heat between said cooling liquid and waste fluid.

4. The steam sterilizer as claimed in claim 1, wherein said cooling means further comprises a vacuum pump configured to cause pressure to decrease in said discharge tank.

5. The steam sterilizer as claimed in claim 1, wherein said cooling apparatus further comprises a cooler configured to cool said sterilization fluid.

* * * * *